(12) United States Patent
Loh et al.

(10) Patent No.: US 7,888,070 B2
(45) Date of Patent: Feb. 15, 2011

(54) NUCLEIC ACIDS ENCODING GROWTH HORMONE WITH A MODIFIED RSP SORTING SIGNAL

(75) Inventors: Yoke Peng Loh, Bethesda, MD (US);
Niamh Cawley, Bethesda, MD (US);
Bruce J. Baum, Bethesda, MD (US);
Christopher R. Snell, Norfolk (GB)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/850,947

(22) Filed: Sep. 6, 2007

(65) Prior Publication Data

US 2008/0008691 A1    Jan. 10, 2008

Related U.S. Application Data

(62) Division of application No. 10/477,651, filed as application No. PCT/US02/15172 on May 14, 2002, now Pat. No. 7,271,150.

(60) Provisional application No. 60/290,836, filed on May 14, 2001.

(51) Int. Cl.
C07H 21/04    (2006.01)
C12N 5/16    (2006.01)
C12N 15/18    (2006.01)
C12N 15/63    (2006.01)

(52) U.S. Cl. .................. 435/69.4; 435/320.1; 435/325; 536/23.51

(58) Field of Classification Search ................ None
See application file for complete search history.

(56) References Cited

U.S. PATENT DOCUMENTS

| | | | |
|---|---|---|---|
| 4,797,368 | A | 1/1989 | Carter et al. |
| 4,816,439 | A | 3/1989 | Jorgensen |
| 5,096,885 | A | 3/1992 | Pearlman et al. |
| 5,426,096 | A | 6/1995 | Sönksen et al. |
| 5,567,677 | A | 10/1996 | Castensson et al. |
| 5,580,723 | A | 12/1996 | Wells et al. |
| 5,587,308 | A | 12/1996 | Carter et al. |
| 5,612,315 | A | 3/1997 | Pikal et al. |
| 5,633,352 | A | 5/1997 | Dalbøge et al. |
| 5,635,604 | A | 6/1997 | Dalbøge et al. |
| 5,654,010 | A | 8/1997 | Johnson et al. |
| 5,667,808 | A | 9/1997 | Johnson et al. |
| 5,734,024 | A | 3/1998 | Zaslavsky |
| 5,763,394 | A | 6/1998 | O'Connor et al. |
| 5,851,992 | A | 12/1998 | Sørensen |
| 5,885,971 | A | 3/1999 | German et al. |
| 5,891,478 | A | 4/1999 | Johnson et al. |
| 5,898,030 | A | 4/1999 | Samaritani |
| 5,981,485 | A | 11/1999 | O'Connor et al. |
| 6,010,999 | A | 1/2000 | Daley et al. |
| 6,013,773 | A | 1/2000 | Kobayashi et al. |
| 6,022,711 | A | 2/2000 | Cunningham et al. |
| 6,051,259 | A | 4/2000 | Johnson et al. |

FOREIGN PATENT DOCUMENTS

| | | |
|---|---|---|
| WO | WO 95/32991 A1 | 12/1995 |
| WO | WO 96/40072 A2 | 12/1996 |
| WO | WO 98/11244 A2 | 3/1998 |
| WO | WO 98/13511 A1 | 4/1998 |
| WO | WO 98/22143 A1 | 5/1998 |
| WO | WO 98/46778 A1 | 10/1998 |
| WO | WO 99/61601 A2 | 12/1999 |
| WO | WO 00/17376 A1 | 3/2000 |
| WO | WO 00/40741 A2 | 7/2000 |

OTHER PUBLICATIONS

Wang et al Hum Gene Ther. May 2005;16(5):571-83. Partial redirection of transgenic human growth hormone secretion from rat salivary glands.*

Baccaglini et al., "Cationic Liposome-mediated Gene Transfer to Rat Salivary Epithelial Cells in vitro and in vivo," *J. Gene. Med.* vol. 3, pp. 82-90 (2001).

Baum et al., "Re-engineering the Functions of a Terminally Differentiated Epithelial Cell in Vivo," *Ann N. Y. Acad. Sci.*, vol. 875, pp. 294-300 (1999).

Becker et al., "Use of Recombinant Adenovirus for Metabolic Engineering of Mammalian Cells," *Methods Cell Biol.*, vol. 43 (Pt A), pp. 161-189 (1994).

Carroll et al., "Growth Hormone Replacement in Adults with Growth Hormone Deficiency: Assessment of Current Knowledge," *Trends Endocrinol. Metab.*, vol. 11 (6), pp. 231-238 (2000).

Carter et al., "Improved Oligonucleotide Site-Directed Mutagenesis Using M13 Vectors," *Nucleic Acids Res.*, vol. 13 (12), pp. 4431-4443 (1985).

Cool et al., "Identification of the Sorting Signal Motif within Proopiomelanocortin for the Regulated Secretory Pathway," *J. Biol. Chem.*, vol. 270 (15), pp. 8723-8729 (1995).

Cool et al., *Cell*, vol. 88, 73-83 (Jan. 10, 1997).

D'Costa et al., "Human Immunodeficiency Virus Type 2 Lentiviral Vectors: Packaging Signal and Splice Donor in Expression and Encapsidation," *J. Gen. Virol.*, vol. 82 (Pt 2), pp. 425-434 (2001).

Delporte et al., "Adenovirus-mediated Expression of Aquaporin-5 in Epithelial Cells," *J. Biol. Chem.*, vol. 271 (36), pp. 22070-22075 (1996).

(Continued)

*Primary Examiner*—Christine J Saoud
(74) *Attorney, Agent, or Firm*—Leydig, Voit & Mayer

(57) ABSTRACT

The invention provides a nucleic acid molecule encoding a growth hormone (GH) in which the RSP sorting signal has been mutated, such that the GH can be constitutively secreted by the nonregulated secretory pathway (NRSP) in a mammalian cell. The invention also provides a nucleic acid molecule encoding a GH in which the three-dimensional conformation of the RSP sorting signal has been altered such that the GH can be constitutively secreted by the NRSP in a mammalian cell.

14 Claims, No Drawings

OTHER PUBLICATIONS

Finidori, "Regulators of Growth Hormone Signaling," *Vitam. Horm.*, vol. 59, pp. 71-97 (2000).

Fisher et al., "A Novel Adenovirus-Adeno-Associated Virus Hybrid Vector that Displays Efficient Rescue and Delivery of the AAV Genome," *Hum. Gene Ther.*, vol. 7, pp. 2079-2087 (1996).

Gorr et al., "Disruption of Disulfide Bonds Exhibits Differential Effects on Trafficking of Regulated Secretory Proteins," *Am. J. Physiol.*, vol. 277, pp. C121-C131 (1999).

He et al., "Systemic Action of Human Growth Hormone Following Adenovirus-Mediated Gene Transfer to Rat Submandibular Glands," *Gene Ther.*, vol. 5, pp. 537-541 (1998).

Lewis et al., "Structure and Properties of Members of the hGH Family: A Review," *Endocr. J.*, vol. 47 (Suppl.), pp. S1-S8 (2000).

Liang et al., "Insulin Receptor Substrate-1 Enhances Growth Hormone-Induced Proliferation," *Endocrinology*, vol. 140 (5), pp. 1972-1983 (1999).

MacGillivray et al., "Outcome of a Four-Year Randomized Study of Daily *Versus* Three Times Weekly Somatropin Treatment in Prepubertal Naive Growth Hormone-Deficient Children," *J. Clin. Endocrinol. Metab.*, vol. 81 (5), pp. 1806-1809 (1996).

Mastrangeli et al., "Direct in vivo Adenovirus-Mediated Gene Transfer to Salivary Glands," *Am. J. Physiol.*, vol. 266, pp. G1146-G1155 (1994).

Mehls et al., "Effects of Recombinant Human Growth Hormone in Catabolic Adults with Chronic Renal Failure," *Growth Horm. IGF Res.*, vol. 10 (Suppl. B), pp. S31-S37 (2000).

Murray et al., "Growth Hormone: Current and Future Therapeutic Applications," *Exp. Opin. Pharmacotherapy*, vol. 1 (5), pp. 975-990 (2000).

O'Connell et al., "Safety and Efficacy of Adenovirus-Mediated Transfer of the Human Aquaporin-1 cDNA to irradiated parotid glands of non-human primates," *Cancer Gene Ther.*, vol. 6 (6), pp. 505-513 (1999).

Parkhurst et al., "Improved Induction of Melanoma-Reactive CTL with Peptides from the Melanoma Antigen gp100 Modified at HLA-A*0201-Binding Residues," *J. Immunol.*, vol. 157, pp. 2539-2548 (1996).

Wang et al., "Adenoviral-mediated Gene Transfer to Mouse Salivary Glands," *J. Dent. Res.*, vol. 79 (2), pp. 701-708 (2000).

Wells et al., "Cassette Mutagenesis: An Efficient Method for Generation of Multiple Mutations at Defined Sites," *Gene*, vol. 34, pp. 315-323 (1985).

Wells et al., "Importance of hydrogen-bond formation in stabilizing the transition state of subtilisin," *Phil. Trans. R. Soc. Lond.*, vol. 317, p. 415-423 (1986).

Wit, "The Use of GH as Pharmacological Agent (minireview)," *Endocr. Regul.*, vol. 33 (1), pp. 28-32 (2000).

Zhang et al., *Mol. Endo.*, 13(4), 527-536 (1999).

Zheng et al., "Genomic Integration and Gene Expression by a Modified Adenoviral Vector," *Nat. Biotechnol.*, vol. 18, pp. 176-180 (2000).

Zoller et al., "Oligonucleotide-Directed Mutagenesis Using M13-Derived Vectors: An Efficient and General Procedure for the Production of Point Mutations in Any Fragment of DNA," *Nucleic Acids Res.*, vol. 10 (20), pp. 6487-6500 (1982).

* cited by examiner

SEQUENCE LISTING

```
<160> NUMBER OF SEQ ID NOS: 3

<210> SEQ ID NO 1
<211> LENGTH: 651
<212> TYPE: DNA
<213> ORGANISM: Homo sapiens

<400> SEQUENCE: 1
atggctacag gctcccggac gtccctgctc ctggcttttg gcctgctctg cctgccctgg      60
cttcaagagg gcagtgcctt cccaaccatt cccttatcca ggcttttga caacgctatg     120 ctccgcgccc atcgtctgca ccagtggcc tttgacacct accaggagtt tgaagaagcc     180
tatatcccaa aggaacagaa gtattcattc ctgcagaacc cccagacctc cctctgtttc     240
tcagagtcta ttccgacacc ctccaacagg gaggaaacac aacagaaatc caacctagag     300
ctgctccgca tctccctgct gctcatccag tcgtggctgg agcccgtgca gtccctcagg     360
agtgtcttcg ccaacagcct ggtgtacggc gcctctgaca gcaacgtcta tgacctccta     420
aaggacctag aggaaggcat ccaaacgctg atggggaggc tggaagatgg cagccccgg      480 actgggcaga tcttcaagca gacctacagc aagttcgaca caaactcaca caacgatgac     540
```

```
gcactactca agaactacgg gctgctctac tgcttcagga aggacatgga caaggtcgag      600
acattcctgc gcatcgtgca gtgccgctct gtggagggca gctgtggctt c              651
```

```
<210> SEQ ID NO 2
<211> LENGTH: 217
<212> TYPE: PRT
<213> ORGANISM: Homo sapiens

<400> SEQUENCE: 2
```

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Ser Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

```
<210> SEQ ID NO 3
<211> LENGTH: 232
<212> TYPE: PRT
<213> ORGANISM: Artificial
<220> FEATURE:
<223> OTHER INFORMATION: Synthetic

<400> SEQUENCE: 3
```

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

-continued

```
Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Ser Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Leu Leu Gly Ile Leu Gln Ile Ser
    210                 215                 220

Ser Thr Val Ala Ala Ala Arg Val
225                 230
```

NUCLEIC ACIDS ENCODING GROWTH HORMONE WITH A MODIFIED RSP SORTING SIGNAL

CROSS-REFERENCE TO RELATED APPLICATIONS

This patent application is a divisional of U.S. patent application Ser. No. 10/477,651, filed Nov. 14, 2003, which is a U.S. National Phase Application of International Patent Application No. PCT/US02/15172 filed May 14, 2002, which claims the benefit of U.S. Provisional Patent Application No. 60/290,836filed May 14, 2001.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,259 Byte ASCII (Text) file named "701849ST25.TXT," created on Aug. 28, 2007.

TECHNICAL FIELD OF THE INVENTION

The present invention relates to modified growth hormone and related compositions, nucleic acids, vectors, isolated host cells comprising such vectors, and methods of manufacture and use.

BACKGROUND OF THE INVENTION

Growth hormone acts through binding to membrane receptors that belong to the cytoidne receptor superfamily (Finidori, Vitam. Horm. 59: 71-97 (2000)). Ligand binding induces receptor dimerization and activation of the receptor-associated kinase JAK-2, resulting in phosphorylation of the kinase, the receptor and many cellular proteins (Finidori (2000), supra). Activation by growth hormone is very transient and several mechanisms are involved in downregulation, including internalization and degradation of the receptor and recruitment of phosphatases or specific inhibitors of the JAK/Stat pathway, namely the SOCS proteins (Finidori (2000), supra).

There are variant forms of human growth hormone (hGH) which include a disulfide dimer, a glycosylated form (20 kD hGH) and two pituitary peptides made up of portions of 22 kD hGH (Lewis et al., Endocr. J. 47 Suppl: S1-8 (March 2000)). The two pituitary peptides (hGH (1-43) and hGH (44-191)) have, respectively, insulin-potentiating and anti-insulin properties (Lewis et al. (March 2000), supra). The smaller peptide may be useful in decreasing the amount of exogenous insulin required by diabetics, whereas the larger peptide may be involved in diabetic retinopathy (Lewis et al. (March 2000), supra).

The increased availability of growth hormone (GH) in the mid-1980s, due to advances in recombinant DNA technology, has allowed research into the use of this hormone at physiological dosage as replacement therapy for adults and children with GH deficiency (GHD) (see, e.g., Carroll et al., Trends Endocrinol. Metab. 11(6): 231-238 (August 2000)) and at pharmacological dosages as a possible therapeutic agent for a number of disease states (Murray et al., Expert Opin. Pharmacother. 1(5): 975-990 (July 2000); see, also, Wit, Endocr. Regul. 34(1): 28-32 (March 2000)). Such disease states include frailty associated with ageing, osteoporosis, morbid obesity, cardiac failure, major thermal injury, hypoglycemic unawareness in diabetes mellitus (Sonksen et al., U.S. Pat. No. 5,426,096, issued Jun. 20, 1995), various acute and chronic catabolic conditions (Murray et al. (July 2000), supra, see, also, Mehls et al., Growth Horm. IGF Res. 10 Suppl. B: S31-37 (April 2000)) and intoxication with poisonous substances that are degraded in the liver by microsomal enzymes (Jorgensen, U.S. Pat. No. 4,816,439, issued Mar. 28, 1989). In combination with DHEA, its use has been proposed for regenerating an involuted thymus (Fahy, International Patent Application WO 95/32991, published Dec. 7, 1995).

GHD in humans is currently treated by growth hormone injection. The problem with such a treatment method is that injections are required every day or couple of days (MacGillivray et al., J. Clin. Endocrinol. Metab. 81(5):1806-1809 (May 1996)). The present invention seeks to overcome such a problem. This and other objects and advantages, as well as additional inventive features, will become apparent from the detailed description provided herein.

BRIEF DESCRIPTION OF THE INVENTION

The present invention provides an isolated and purified GH in which the regulated secretory pathway (RSP) sorting signal has been mutated as well as an isolated and purified ( GH in which the three-dimensional conformation of the RSP sorting signal has been altered. Also provided is a composition comprising an effective amount of such an isolated and purified GH in an excipient.

Further provided is an isolated and purified nucleic acid molecule encoding GH in which the RSP sorting signal has been mutated such that the GH can be constitutively secreted by the nonregulated secretory pathway (NRSP) in a mammalian cell as well as an isolated and purified nucleic acid molecule encoding GH in which the three-dimensional conformation of the RSP sorting signal has been altered such that the GH can be constitutively secreted by the NRSP in a mammalian cell. Still further provided are a vector comprising such an isolated and purified nucleic acid molecule and an isolated host cell comprising such a vector.

A method of treating GHD in a mammal is also provided. The method comprises administering to the mammal the aforementioned composition, nucleic acid or vector, wherein the nucleic acid or vector expresses an effective amount of the encoded GH and whereupon GHD in the mammal is treated.

Also provided are a method of making a GH in which the RSP sorting signal is mutated and the GH so produced. The method comprises mutating one or more amino acids in the RSP sorting signal in GH, whereupon a GH in which the RSP sorting signal is mutated is obtained.

Still also provided are a method of making a GH in which the three-dimensional conformation of the RSP sorting signal is altered and the GH so produced. The method comprises mutating one or more amino acids outside of the RSP sorting signal so that the three-dimensional conformation of the amino acids of the RSP sorting signal in GH is altered, whereupon a GH with an RSP having an altered three-dimensional conformation is obtained.

Similarly provided is a method of making a nucleic acid molecule encoding a GH that can be constitutively secreted by the NRSP in a mammalian cell and the nucleic acid molecule so produced. The method comprises mutating one or more codons encoding amino acids in the RSP sorting signal in an isolated and purified nucleic acid molecule encoding GH such that, upon expression in a mammalian cell, the GH can be constitutively secreted by the NRSP in a mammalian cell.

Also similarly provided is a method of making a nucleic acid molecule encoding a GH that can be constitutively secreted by the NRSP in a mammalian cell and the nucleic acid molecule so produced. The method comprises mutating one or more codons encoding amino acids outside of the RSP sorting signal in an isolated and purified nucleic acid molecule encoding GH such that the three-dimensional conformation of the amino acids of the RSP sorting signal in GH is altered and, upon expression in a mammalian cell, the GH can be constitutively secreted by the NRSP in a mammalian cell.

DETAILED DESCRIPTION OF THE INVENTION

The present invention provides an isolated and purified GH in which the RSP sorting signal has been mutated. Any GH can be modified in accordance with the present invention. Preferably, the GH is mammalian. Particularly preferred is hGH. The amino acid sequence of hGH is known (Genbank accession no. A 15072; see also biosynthetic hGH of Dalboge et al., U.S. Pat. No. 5,633,352, issued May 27, 1997, and U.S. Pat. No. 5,635,604, issued Jun. 3, 1997) and is reproduced herein as SEQ ID NO: 2. By "mutated" is meant chemical modification, substitution, deletion or insertion. Methods of chemical modification, substitution, deletion and insertion are known in the art and include in vitro chemical synthesis (e. g., Merrifield synthesis) of the desired mutant GH (see, e. g., Barany et al., in *The Peptides*, Gross and Meienhofer, eds. Academic Press: New York (1979), Vol. 2, pp. 3-254; and Parkhurst et al., J. Immunol. 157: 2539-2548 (1996)). Substitution is preferred. Preferably, the isolated and purified GH consists essentially of the amino acid sequence of SEQ ID NO: 2 in which the sorting signal comprises glutamic acid at amino acid position 174 (Glu 174), leucine at amino acid position 177 (Leu 177), valine at amino acid position 185 (Val 185) and glutamic acid at amino acid position 186 (Glu 186) and one or more of the aforementioned amino acids is mutated. Preferably, each of Glu 174 and Glu 186 is mutated, preferably by substitution with alanine.

Especially preferred is when the isolated and purified GH consists essentially of the amino acid sequence of SEQ ID NO: 2 in which the sorting signal comprises glutamic acid at amino acid position 174 (Glu 174), leucine at amino acid position 177 (Leu 177), valine at amino acid position 185 (Val 185) and glutamic acid at amino acid position 186 (Glu 186), each of Glu 174 and Glu 186 is substituted with alanine, and Phe 191 is substituted with LLGILQISSTVAAARV (SEQ ID NO: 3). Optionally, Leu 177 and/or Val 185 is/are mutated, such as by substitution.

Also provided is an isolated and purified GH in which the three-dimensional conformation of the RSP sorting signal has been altered. Preferably, the isolated and purified GH consists essentially of the amino acid sequence of SEQ ID NO: 2 in which the sorting signal comprises Glu 174, Leu 177, Val 185 and Glu 186 and in which one or more amino acids outside of the RSP sorting signal is mutated. Preferably, the cysteine at amino acid position 189 (Cys 189) is mutated, preferably by substitution with serine.

While the above-described mutations are preferred, other mutations that either interfere with the charge of the acidic residues or alter the three-dimensional conformation of the sorting signal are possible. For example, a positively charged residue(s), such as arginine or lysine, can be introduced close to or beside either one or both of the glutamic acid residues in order to neutralize the acidic charge of the neighboring glutamic acid residue. Alternatively, a proline residue can be introduced near the sorting signal so as to alter the three-dimensional conformation of the sorting signal region.

In view of the above, the present invention also provides a composition comprising an effective amount of an above-described isolated and purified GH in an excipient, such as a vehicle, adjuvant, carrier or diluent, which is desirably pharmaceutically acceptable, as known in the art. See, for example, *Pharmaceutics and Pharmacy Practice*, J. B. Lippincott Co., Philadelphia, Pa., Banker and Chalmers, eds. (1982), and ASHP Handbook on Injectable Drugs, Toissel, 4th ed. (1986).

Such compositions can further comprise asparagine (Sorensen, U.S. Pat. No. 5,851,992, issued Dec. 22, 1998). Injectable aqueous formulations, such as those which comprise a buffer, nonionic surfactants and neutral salts are known in the art (see, e.g., O'Connor et al., U.S. Pat. No. 5,763,394, issued Jun. 9, 1998; and U.S. Pat. No. 5,981,485, issued Nov. 9, 1999). Sustained-release compositions, such as those comprising GH complexed with a metal, such as zinc, are described by Johnson et al. (U.S. Pat. No. 5,667,808, issued Sep. 16, 1997). Metal-complexed GH can be further combined with a biocompatible polymer (see, e.g., Johnson et al., U.S. Pat. No. 5,654,010, issued Aug. 5, 1997; U.S. Pat. No. 5,891,478, issued Apr. 6, 1999; U.S. Pat. No. 6,051,259, issued Apr. 18, 2000; and International Patent Application WO 96/40072). Glycine and mannitol also can be used to stabilize GH for parenterally administered formulations (see, e.g., Pikal et al., U.S. Pat. No. 5,612,315, issued Mar. 18, 1997; and Pearlman et al., U.S. Pat. No. 5,096,885, issued Mar. 17, 1992). Saccharose, alone or in further combination with mannitol, can be used to stabilize GH as a solid intimate mixture (see, e.g., Samaritani, U.S. Pat. No. 5,898,030, issued Apr. 27, 1999). Injectable GH formulations which comprise citrate can be stable for at least 12 months (see, e.g., Castensson et al., U.S. Pat. No. 5,567,677, issued Oct. 22, 1996). Solubility of GH in an aqueous solution can be enhanced by the presence of creatinine, an acetyl tryptophan salt and/or nicotinamide (see, e.g., U.S. Pat. No. 6,013,773, issued Jan. 11, 2000).

Also in view of the above, the present invention provides an isolated and purified nucleic acid molecule encoding GH in which the RSP sorting signal has been mutated such that the hGH can be constitutively secreted by the nonregulated secretory pathway (NRSP) in a mammalian cell. Any nucleic acid molecule encoding a GH can be modified in accordance with the present invention. Preferably, the GH is mammalian. Particularly preferred is hGH. The nucleotide sequence of hGH is known (Genbank accession no. A 15072) and is reproduced herein as SEQ ID NO:1. Methods of introducing mutations at the nucleic acid level are known in the art and include the methods of Example 1, site-specific mutagenesis (Carter et al., Nucl. Acids Res. 13: 4331 (1986); and Zoller et al., Nucl. Acids Res. 10: 6487 (1987)), cassette mutagenesis (Wells et al., Gene 34: 315 (1985)), restriction selection mutagenesis (Wells et al., Philos. Trans. R. Soc. London SerA 317: 415 (1986)) and DNA synthesis of the mutated GH. When modifying the nucleic acid so that a new amino acid is substituted for that which is naturally occurring, the codon encoding the amino acid sequence to be substituted may be any of the alternative codons known to code for the particular amino acid (see, e. g. Lewin, GENES V, Oxford University Press, page 172 (1994)). For example, when the desired substitution is to result in the amino acid alanine, the codons which could be used include GCT, GCC, GCA or GCG. Substitution is preferred. Preferably, the isolated and purified nucleic acid molecule encodes the amino acid sequence of SEQ ID NO:2 in which the sorting signal comprises Glu 174, Leu 177, Val 185 and Glu 186 and one or more of the codons encoding the aforementioned amino acids is mutated. Preferably, each of the codons encoding Glu 174 and Glu 186 is mutated, preferably mutated to encode alanine.

Especially preferred is when the isolated and purified nucleic acid molecule encodes the amino acid sequence of SEQ ID NO: 3. Optionally, the isolated and purified nucleic acid molecule encodes a mutation of Leu 177 and/or Val 185, such as a substitution.

Still also in view of the above, the present invention provides an isolated and purified nucleic acid molecule encoding GH in which the three-dimensional conformation of the RSP sorting signal has been altered such that the GH can be constitutively secreted by the NRSP in a mammalian cell. Preferably, the isolated and purified nucleic acid molecule encodes the amino acid sequence of SEQ ID NO: 2 in which the sorting signal comprises Glu 174, Leu 177, Val 185 and Glu 186 and one or more of the codons encoding amino acids outside of the sorting signal is mutated. Preferably, the codon encoding Cys 189 is mutated, preferably mutated to encode serine.

A vector comprising an above-described isolated and purified nucleic acid molecule is also provided. Vectors and vector construction are known in the art (see, e.g., Maniatis et al., *Molecular Cloning: A Laboratory Manual*, Cold Spring Harbor Laboratory, NY (1982)). Preferred vectors for use in the context of the present invention include adenoviral vectors and adeno-associated viral (AAV) vectors. AAV vectors have been developed for a number of AAV serotypes, including AAV2 (see, e.g., Carter et al., U.S. Pat. No. 4,797,368, issued Jan. 10, 1989, and U.S. Pat. No. 5,587,308, issued Dec. 24, 1996), AAV4 (see, e.g., Chiorini et al., International Patent Application WO 98/11244, published Mar. 19, 1998) and AAV5 (see, e.g., Chiorini, et al. WO 99/61601 published Dec. 2, 1999). Other vectors which may be usefull include lentivirus-based vectors (see, e.g., D'Costa et al., J. Gen. Virol. 82(Pt 2): 425-434 (February 2001); Arya, International Patent Application WO 00/40741, published Jul. 13, 2000; and Morgan et al., International Patent Application WO 98/13511, published Apr. 2, 1998) and hybrid or chineric viral vectors or vector systems comprising, for example, an adenoviral backbone with lentiviral components (see, e.g., Zheng et al., Nature Biotechnology 18(2): 176-80 (February 2000); Curiel et al., International Patent Application WO 98/22143, published May 28, 1998; Ramsey et al., International Patent Application WO 98/46778, published Oct. 22, 1998; and Ramsey et al., International Patent Application WO 00/17376, published Mar. 30, 2000), or an adenoviral backbone with AAV components (Fisher et al., Human Gene Therapy 7: 2079-2087 (1996)). While the promoter native to hGH can be used, preferably a nonnative promoter is used. Examples of such nonnative promoters include various constitutive and regulatable promoters. Examples of regulatable promoters include inducible, repressible and tissue-specific promoters. Specific examples include viral promoters, preferable adenoviral promoters and AAV promoters, and a promoter that is specific for expression in the salivary gland, such as the promoter from the amylase gene. Preferably, the promoter is an adenoviral promoter.

Accordingly, an isolated host cell comprising the above-described vector is also provided. Any suitable host cell can be used. Examples include prokaryotic host cells, such as *E. coli*, in particular K12 strain 294 (American Type Culture Collection (ATCC) No. 31446), B, X1776 (ATCC No. 31537), c600, c600hfl, W3110 (ATCC No. 27,325), JM101, HB101, NM522, NM538 and NM539, *Bacillus subtilis, Salmonella typhimuriuni, Serratia marcescens*, and *Pseudomonas*. Eukaryotic host cells include, for example, yeast and cells derived from a mammal, including human cell lines. Specific examples of suitable eukaryotic host cells include VERO, HeLa, 3T3, Chinese hamster ovary (CHO) cells, W138 BHK, COS-7 and MDCK. Alternatively, cells from a human to be treated in accordance with the methods described herein can be used as host cells. Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., *Molecular Biology: A Laboratory Manual*, Cold Spring Harbor Laboratory, NY (1989); Davis et al., *Basic Methods in Molecular Biology* (1986), and Neumann et al., EMBO J. 1: 841 (1982)).

The form of the introduced vector can vary with the rationale underlying the introduction of the vector into the host cell. For example, the nucleic acid can be closed circular, nicked, or linearized, depending on whether the vector is to be maintained extragenomically (i.e., as an autonomously replicating vector), integrated as a provirus or prophage, transiently transfected, transiently infected as with use of a replication-deficient or conditionally replicating virus or phage, or stably introduced into the host genome through double or single crossover recombination events.

In addition to the above, the present invention provides a method of treating GHD in mammals, in particular a human. In one embodiment, the method comprises administering to the mammal an above-described composition, whereupon the GHD in the mammal is treated. While any species of mammal can be used as the source of the GH, desirably the GH is from the same species as the mammal being treated. Any suitable route of administration can be used in the context of this method, including local and systemic administration, such as parenteral, i.e., subcutaneous, intramuscular, intravenous, intraarterial and intraperitoneal administration. Preferably, the composition is administered to the mammal by subsutaneous injection to the mammal. In another embodiment, the method comprises administering to the mammal an above-described nucleic acid or vector that expresses an effective amount of the encoded GH, whereupon the GHD in the mammal is treated. As indicated above, while any species can be used as the source of nucleic acid encoding GH, desirably the GH is from the same species as the mammal being treated. While any suitable route of administration can be used in the context of this method, preferably, the vector is administered to the mammal in vio, such as by infusion via the main excretory ducts of the salivary gland ("salivary gland" includes glandulae salivariae majores (parotid, sublingual and submandibular glands) and glandulae salivariae minores of the tongue, lips, cheeks and palate (labial, buccal, molar, palatine, lingual and anterior lingual glands)) of the mammal (see, e.g., Example 4 and the references cited therein and German et al., U.S. Pat. No. 5,885,971, issued Mar. 23, 1999). Alternatively, an above-described nucleic acid or vector encoding GH in accordance with the present invention can be contacted with host cells ex vivo and subsequently administered to the mammal to be treated. Preferably, the host cells are autologous cells, such as biopsied secretory gland tissue, e.g., salivary gland tissue (see, e.g., German et al., supra).

Generally, the effective amount of modified GH administered parenterally per dose is in the range of about 1 µg/kg body weight/day to about 100 µg/kg body weight/day. Usually, the effective amount of modified GH administered parenterally per dose is in the range of about 0.01 mg/kg body weight/day and 10 mg/kg body weight/day. Even more usually, the effective amount of modified hGH administered parenterally per dose is in the range of about 0.01 µg/kg/day and 1 µg/kg/day. If given continuously, the modified GH is typically administered at a dose rate of about 1 µg/kg body weight/hr to about 50 µg/kg body weight/hr, such as by one to four injections per day or by continuous subcutaneous infusions. Administration can be repeated daily, three times per week, every three days or once a month. Typically, administration is repeated about once a day to every 2-3 days.

Desirably, an above-described vector that expresses an effective amount of modified GH is administered. When an above-described nucleic acid or vector is administered to the salivary gland, from about 1 µg to 200 mg, preferably from about 100 µg to 100 mg, more preferably from about 500 µg to 50 mg, most preferably about 10 mg, of vector are administered. If the vector is a viral vector, preferably a tissue concentration of about $10^2$ to about $10^{12}$ viral particles per ml is attained. Generally, the amount of vector necessary can be extrapolated from animal models. For example, the amount of DNA to be administered to a human is about 10-100 times the amount of DNA to be administered to a rat. Use of an adequate vector, which is preferably a viral vector, obviates the need for frequent repeat administrations. When a vector is administered, the vector is preferably administered once or up to about once per month The present inventive method of treatment can be used to treat other conditions or disease states in addition to GHD in which the administration of hGH would be beneficial. For example, the method can be used to treat frailty associated with ageing, osteoporosis, morbid obesity, cardiac failure, major thermal injury, hypoglycemic unawareness in diabetes mellitus (Sonksen et al. (Jun. 20, 1995), supra), various acute and chronic catabolic conditions (Murray et al. (July 2000), supra; Mehls et al. (April 2000), supra) and intoxication with poisonous substances that are degraded in the liver by microsomal enzymes (Jorgensen (Mar. 28, 1989), supra).

A method of making a GH in which the RSP sorting signal is mutated is also provided. The method comprises mutating one or more amino acids in the RSP sorting signal in GH, whereupon a GH in which the RSP sorting signal is mutated is obtained. As indicated above, methods of mutating amino acids are known in the art. Accordingly, a GH with a mutated RSP sorting signal obtained in accordance with such a method is also provided.

Further provided is a method of making a GH in which the three-dimensional conformation of the RSP sorting signal is altered. The method comprises mutating one or more amino acids outside of the RSP sorting signal so that the three-dimensional conformation of the amino acids of the RSP sorting signal in GH is altered, whereupon a GH with an RSP having an altered three-dimensional conformation is obtained. Methods of mutating amino acids are known in the art as indicated above. Accordingly, a GH with an RSP sorting signal having an altered three-dimensional conformation obtained in accordance with such a method is also provided.

Still further provided is a method of making a nucleic acid molecule encoding a GH that can be constitutively secreted by the NRSP in a mammalian cell. The method comprises mutating one or more codons encoding amino acids in the RSP sorting signal in an isolated and purified nucleic acid molecule encoding GH such that, upon expression in a mammalian cell, the GH can be constitutively secreted by the NRSP in the mammalian cell. As indicated above, methods of introducing mutations at the nucleic acid level are known in the art. Accordingly, a nucleic acid molecule encoding a GH with a mutated RSP sorting signal obtained in accordance with such a method is also provided.

Yet still further provided is a method of making a nucleic acid molecule encoding a GH that can be constitutively secreted by the NRSP in a mammalian cell. The method comprises mutating one or more codons encoding amino acids outside of the RSP sorting signal in an isolated and purified nucleic acid molecule encoding GH such that the three-dimensional conformation of the amino acids of the RSP sorting signal in GH is altered and, upon expression in a mammalian cell, the GH can be constitutively secreted by the NRSP in the mammalian cell. Methods of introducing mutations at the nucleic acid level are known in the art as indicated above. Accordingly, a nucleic acid molecule encoding a GH with an RSP sorting signal having an altered three-dimensional conformation obtained in accordance with such a method is also provided.

Whether or not a recombinantly produced GH is secreted by the NRSP in a mammalian cell and has biological activity can be determined in accordance with the methods set forth in the Examples. An alternative method of determining the biological activity of recombinantly produced GH is described in Zaslavsky, U.S. Pat. No. 5,734,024, issued Mar. 31, 1998.

EXAMPLES

The following examples serve to illustrate further the present invention and are not intended to limit its scope in any way.

Example 1

This example demonstrates the existence of an RSP sorting signal in hGH and describes the essential amino acid residues of the RSP sorting signal motif and their mutation leading to constitutive secretion of hGH.

Experimental data have evidenced the existence of RSP sorting signals in pro-opiomelanocortin (POMC; see, e.g., Cool et al., J. Biol. Chem. 270(15): 8723-8729 (Apr. 14, 1995)) and chromogranin B. Thus, hGH was examined for the presence of an RSP sorting signal.

Initially, the amino acid sequences of growth hormones from multiple species were analyzed to identify evolutionarily conserved amino acids. Since the RSP sorting signals of POMC and chromogranin B included acidic residues, acidic residues in the conserved amino acid sequences were identified.

The X-ray crystal structure of hGH (Brookhaven Protein Database accession no. 1HGU) was then analyzed to determine if the conserved amino acids were exposed on the surface of the molecule and, therefore, accessible to the sorting receptor. Since NMR structural data were available for POMC and the molecular distances between the amino acids of the POMC sorting signal were known, several exposed amino acid residues in hGH having similar molecular distances to those of POMC were selected. The selected amino acid residues were in a region of the hGH molecule that was not involved in the binding of hGH to the physiological GH receptor so as to maintain biological activity for physiological signal transduction.

Molecular distances between amino acid residues of the proposed RSP sorting signal in hGH as compared to the molecular distances between amino acid residues of the RSP sorting signal in POMC

| | POMC | hGH |
|---|---|---|
| Acidic residue 1 (Asp10 for POMC; Glu174 for hGH) to hydrophobic residue 1 (Leu11 for POMC; Leu177 for hGH) | 3.82 | 4.57 |
| Acidic residue 2 (Glu14 for POMC; Glu186 for hGH) to hydrophobic residue 2 (Leu18 for POMC; Leu185 for hGH) | 9.29 | 3.79 |
| Acidic residue 1 (Asp10 for POMC; Glu174 for hGH) to acidic residue 2 (Glu14 for POMC; Glu186 for hGH) | 11.6 | 17.59 |

Molecular distances are in Angstroms measured between the alpha carbons of each indicated amino acid. The data for growth hormone were obtained from its X-ray crystal structure and the data for POMC were obtained from its NMR structure.

The molecular distances between the amino acid residues of hGH as compared to POMC were sufficiently variable so as to require experimental proof of a sorting signal for hGH. The selected amino acid residues were tested empirically for their ability to direct hGH to the RSP by mutating them and assaying for secretion. Mutants were generated as follows. The wild-type hGH was generated by reverse-transcriptase polymerase chain reaction (RT-PCR) from a human pituitary cDNA library (Clontech, Palo Alto, Calif.) using a kit from Boehringer-Mannheim (Indianapolis, Ind.). The hGH cDNA was directionally subcloned into a mammalian expression vector, pcDNA3.1 (InVitrogen, Carlsbad, Calif.). The plasmid was used as the template for mutagenesis.

Mutagenesis was performed using the Quick Change mutagenesis kit (Stratagene, LaJolla, Calif.). Briefly, oligonucleotide primers bearing the mutant nucleotide were used in a PCR reaction to amplify the pcDNA3.1-hGH plasmid. The parental DNA was then digested with the restriction endonuclease, Dpn 1. The remaining amplified DNA was transformed into a special strain of E. coli (from Stratagene) and cultured Colonies were picked and the plasmid DNA isolated from the colonies was sequenced to confirm that they contained the mutations. For double mutants, a second round of mutagenesis with new mutant primers was carried out using the first mutant as the PCR template.

The two acidic residues that caused mis-sorting to the constitutive pathway were Glu 174 and Glu 186 and, thus, were determined to be an essential part of the sorting signal motif. Mutation of these glutamic acid residues to alanines, thereby removing the negative charges associated with these residues without causing major structural changes in the loop structure of the sorting signal motif resulted in mis-sorting to the constitutive pathway (i.e., NRSP). It was also determined that mutation of Cys 189 in the loop disrupted stability afforded by the disulfide bridge between Cys 189 and Cys 182. Mutations of either or both of the two cysteine residues can affect the three-dimensional conformation of the loop structure of the sorting signal motif by causing unfolding of the C-terminal loop, thereby disrupting the alignment of the acidic residues necessary for sorting via the RSP.

Example 2

This example describes a method of assaying mutant GH for secretion.

The RSP in (neuro)-endocrine cells can be stimulated to release the peptide hormones that are stored within the cells. The mechanism for stimulating these cells is widely used. Typically, this is done by depolarizing the plasma membrane by adding 50 mM $K^+$ to the medium in the presence of calcium. Alternatively, specific chemicals or other proteins (or peptides) can be added to the medium that bind to a receptor on the plasma membrane and cause stimulated secretion via signal transduction. Primarily, a depolarizing procedure based on the procedure described in Gorr et al., Am. J. Physiol. 277: C121-131 (1999), was used.

Plasmids of pcDNA3.1-GH or pcDNA3.1-mutant-GH were transiently transfected into PC12 or AtT20 cells, which are model (neuro)-endocrine cell lines that contain both a regulated and a constitutive secretory pathway. Forty-eight hours after transfection with lipofectamine 2000 (Gibco BRL, Rockville, Md.), the PC12 cells were pre-incubated twice in a basal buffer (129 mM NaCl, 10 mM HEPES, 5 mM $NaHCO_3$, 4.8 mM KCl, 2.8 mM Glucose, 1.2 mM $KH_2PO_4$, 1.2 mM $MgCl_2$, and 1 mM $CaCl_2$, pH 7.4) for 15 and 30 minutes, respectively. Afterwards, the cells were incubated in 1 ml of fresh basal buffer for 2 hr. This buffer (M1) was then saved for Western blot analysis and replaced with either of the same volume of basal buffer or stimulation buffer (same as basal buffer but with 79 mM NaCl, 50 mM KCl, 2 mM $BaCl_2$ and no $CaCl_2$) and incubated for 10 min. This buffer ($M2^-$ and $M2^+$) was also saved for Western blot analysis. Immediately upon collection of either of the basal or stimulation buffers, they were centrifuged at 1000×g to remove cell debris prior to being processed for Western blot analysis. The cells were washed twice with PBS and then harvested in 1 ml of lysis buffer (50 mM HEPES, 150 mM NaCl, 10 mM EDTA, 10 mM sodium pyrophosphate, 100 mM NaF, 2 mM sodium orthovanadate, 1% Triton X-100, Boehringer Mannheim complete mini protease cocktail, and 1 μM pepstatin A, pH 7.5). A soluble cell extract (L) was obtained from the lysate after three freeze-thaw cycles and centrifugation at 13,000 rpm for 10 min. The levels of GH in the media and lysates were detected by Western blot analysis and/or radioimmunoassay (RIA).

Example 3

This example describes a method of assaying mutant GH for bioactivity.

32D-rGHR-IRS-1 are special cells that have been engineered to express the rabbit growth hormone receptor (rGHR) and an insulin response substrate (IRS) (Liang et al., Endocrinology 140: 1972-1983 (1999)). These cells were provided by Dr. Stuart J. Frank, University of Alabama. These cells require GH to survive through the action of the rabbit GH receptor. They normally get sufficient GH to survive from fetal bovine serum, which is added to the regular culture medium.

In order to test the bioactivity of the GH mutants, the 32D-rGHR-IRS-1 cells were starved of serum for 5 hr and then plated into a 24-well plate. Control serum-free medium, GH standards (purified protein), and expressed GH (wild-type or mutants in conditioned medium) were separately added to the serum starved cells and the cells were allowed to grow for 12-16 hr. The number of viable cells remaining in the wells was then quantified by trypan blue exclusion. Dead cells absorb the blue dye, whereas viable cells actively exclude the dye. In the presence of either GH standard or any GH expressed from the wild-type or mutant constructs, the number of viable cells remained high. In the presence of serum-free medium that contained no GH, the number of viable cells was dramatically reduced. Thus, the mutant GH proteins were biologically active. In addition, the mutants appeared to be as biologically active as wild-type GH.

Example 4

This example describes a method of using an adenoviral vector to transfer a gene encoding mutant GH to a salivary gland of a mammal in vivo.

Adenoviral vectors were constructed in accordance with the methods of Becker et al., Methods Cell. Biol. 43 Pt A: 161-189 (1994); Delporte et al., J. Biol. Chem. 271: 22070-22075 (1996); and He et al., Gene Therapy 5: 537-541 (1998). "First generation" recombinant adenoviruses (serotype 5, E1-deleted) were used. The adenoviral vectors encoding mutant GH were transferred to salivary glands, such as parotids, submandibular glands and sublingual glands, by retrograde infusion following cannulation of the main excretory ducts (see, e.g., Mastrangeli et al., Am. J. Physiol. 266: G1146-G1155 (1994); Baum et al. Ann. N.Y. Acad. Sci. 875: 294-300 (1999); Baccaglini et al., J. Gene. Med 3: 82-90 (2001); Wang et al., J. Dental Res. 79: 701-708 (1999); and O'Connell et al., Cancer Gene Ther. 6: 505-513 (1999)).

Amino acid designations in the specification reference the mature hGH protein, whereas SEQ ID NO: 2 is the amino acid sequence of the precursor hGH protein.

Cys 189 in mature hGH is Cys 215 in precursor hGH of SEQ ID NO: 2.

Glu 186 in mature hGH is Glu 212 in precursor hGH of SEQ ID NO: 2.

Val 185 in mature hGH is Val 211 in precursor hGH of SEQ ID NO: 2.

Glu 174 in mature hGH is Glu 200 in precursor hGH of SEQ ID NO: 2.

Leu 177 in mature hGH is Leu 203 in precursor hGH of SEQ ID NO: 2.

Phe 191 in mature hGH is Phe 217 in precursor hGH of SEQ ID NO: 2.

All references, including publications, patent applications, and patents, cited herein are hereby incorporated by reference to the same extent as if each reference were individually and specifically indicated to be incorporated by reference and were set forth in its entirety herein.

All amino acid numbering herein is based on the mature proteins. The amino acids are numbered consecutively from the N-terminus to the C-terminus of the mature protein starting with "1" in accordance with convention.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated and purified nucleic acid molecule of which encodes the amino acid sequence of SEQ ID NO: 2, wherein nucleotides encoding amino acids Glu 200, and Glu 212 are mutated to encode another amino acid, and optionally, the nucleotides encoding amino acids Leu 203 and/or Val 211 are mutated to encode another amino acid.

2. The isolated and purified nucleic acid molecule of claim 1, in which the nucleotides encoding Glu 200 and Glu 212 are mutated to encode alanine.

3. The isolated and purified nucleic acid molecule of claim 2, in which the nucleotides encoding Phe 217 are substituted with nucleotides encoding LLGILQISSTVAAARV (SEQ ID NO: 3) and, optionally, nucleotides encoding Leu 203 and/or Val 211 are mutated to encode another amino acid.

4. The isolated and purified nucleic acid molecule of claim 3, in which the nucleotides encoding Leu 203 and/or Val 211 are mutated to encode another amino acid.

5. A vector comprising the isolated and purified nucleic acid molecule of claim 1.

6. An isolated host cell comprising the vector of claim 5.

7. An isolated and purified nucleic acid molecule encoding a GH precursor protein having the amino acid sequence of SEQ ID NO:2, in which the three-dimensional conformation of the RSP sorting signal has been altered, wherein two or more of the nucleotides encoding Glu 200, Leu 203, Val 211 and Glu 212 are mutated to encode another amino acid, such that a mature GH can be constitutively secreted by the NRSP in a mammalian cell.

8. The isolated and purified nucleic acid molecule of claim 7, in which the nucleotides encoding Cys 215 are mutated to encode another amino acid.

9. The isolated and purified nucleic acid molecule of claim 8, in which the nucleotides encoding Cys 215 are mutated to encode serine.

10. A vector comprising the isolated and purified nucleic acid molecule of claim 7.

11. An isolated host cell comprising the vector of claim 10.

12. An isolated and purified nucleic acid molecule which encodes the amino acid sequence of SEQ ID NO: 2, wherein the nucleotides encoding amino acids Glu 200 or Glu 212 are mutated to encode another amino acid, and wherein the nucleotides encoding amino acids Leu 203 and/or Val 211 are mutated to encode another amino acid.

13. The isolated and purified nucleic acid molecule of claim 12, in which the nucleotides encoding Glu 200 or Glu 212 are mutated to encode alanine.

14. The isolated and purified nucleic acid molecule of claim 12, in which the nucleotides encoding Leu 203 and Val 211 are mutated to encode another amino acid.

* * * * *